US00PP23670P2

(12) United States Plant Patent
Ingram

(10) Patent No.: US PP23,670 P2
(45) Date of Patent: Jun. 18, 2013

(54) ***SWIETENIA* TREE NAMED 'INGRAM'S RED'**

(50) Latin Name: *Swietenia mahagoni*
Varietal Denomination: Ingram's Red

(75) Inventor: William B. Ingram, Homestead, FL (US)

(73) Assignee: Doug Ingram and Sons Nursery LLC, Homestead, FL (US)

( * ) Notice: Subject to any disclaimer, the term of this patent is extended or adjusted under 35 U.S.C. 154(b) by 66 days.

(21) Appl. No.: 13/373,819

(22) Filed: Dec. 1, 2011

(51) Int. Cl.
*A01H 5/00* (2006.01)

(52) U.S. Cl.
USPC ..... Plt./216

(58) Field of Classification Search
USPC ..... Plt./216
See application file for complete search history.

*Primary Examiner* — Annette Para
(74) *Attorney, Agent, or Firm* — Penny J. Aguirre

(57) ABSTRACT

A new cultivar of *Swietenia mahagoni* named 'Ingram's Red', characterized by its foliage on new wood that is dark burgundy to maroon in color, its small leaves with red petioles and rachis, its leaflets that have red petiolules and red midrib veins, its new wood that is red in color, and its dwarf growth habit.

2 Drawing Sheets

Botanical classification: *Swietenia mahagoni.*
Variety denomination: 'Ingram's Red'.

BACKGROUND OF THE INVENTION

The present invention relates to a new and distinct cultivar of *Swietenia mahagoni*, and will be referred to hereafter by its cultivar name, 'Ingram's Red'. 'Ingram's Red' is a new cultivar of West Indies mahagony tree grown for use as a landscape plant.

The new cultivar of *Swietenia*, 'Ingram's Red', was discovered by the Inventor in spring of 1996 in Homestead, Fla. as a naturally occurring whole plant mutation. 'Ingram's Red' was discovered in a nursery bed of seedlings derived from seed of unnamed plants of *Swietenia mahagoni.*

Asexual reproduction of the new cultivar was first accomplished by stem cuttings by the Inventor in Homestead, Fla. in May 2000. The characteristics of this cultivar have been determined to be stable and are reproduced true to type in successive generations.

SUMMARY OF THE INVENTION

The following traits have been repeatedly observed and represent the characteristics of the new cultivar as grown outdoors in Homestead, Fla. These attributes in combination distinguish 'Ingram's Red' as a unique cultivar of *Swietenia.*

1. 'Ingram's Red' exhibits foliage on new wood that is dark burgundy to maroon in color.
2. 'Ingram's Red' exhibits leaves that are smaller in size than is typical of the species.
3. 'Ingram's Red' exhibits leaves that have red petioles and rachis.
4. 'Ingram's Red' exhibits leaflets that have red petiolules and red midrib veins.
5. 'Ingram's Red' exhibits new wood that is red in color.
6. 'Ingram's Red' exhibits a dwarf growth habit.

Plants of parental species, *Swietenia mahagoni*, differ from 'Ingram's Red' in having green foliage and new wood and in lacking any red coloration in its foliage and wood. In addition, 'Ingram's Red' has a dwarf plant habit in comparison. There are no other cultivars of *Swietenia mahagoni* known to the Inventor.

BRIEF DESCRIPTION OF THE DRAWING

The accompanying colored photographs illustrates the overall appearance and distinct characteristics of an eleven year-old tree the new *Swietenia* as grown outdoors in a 200-gallon container in Homestead, Fla.

The photograph is

Figure 1:
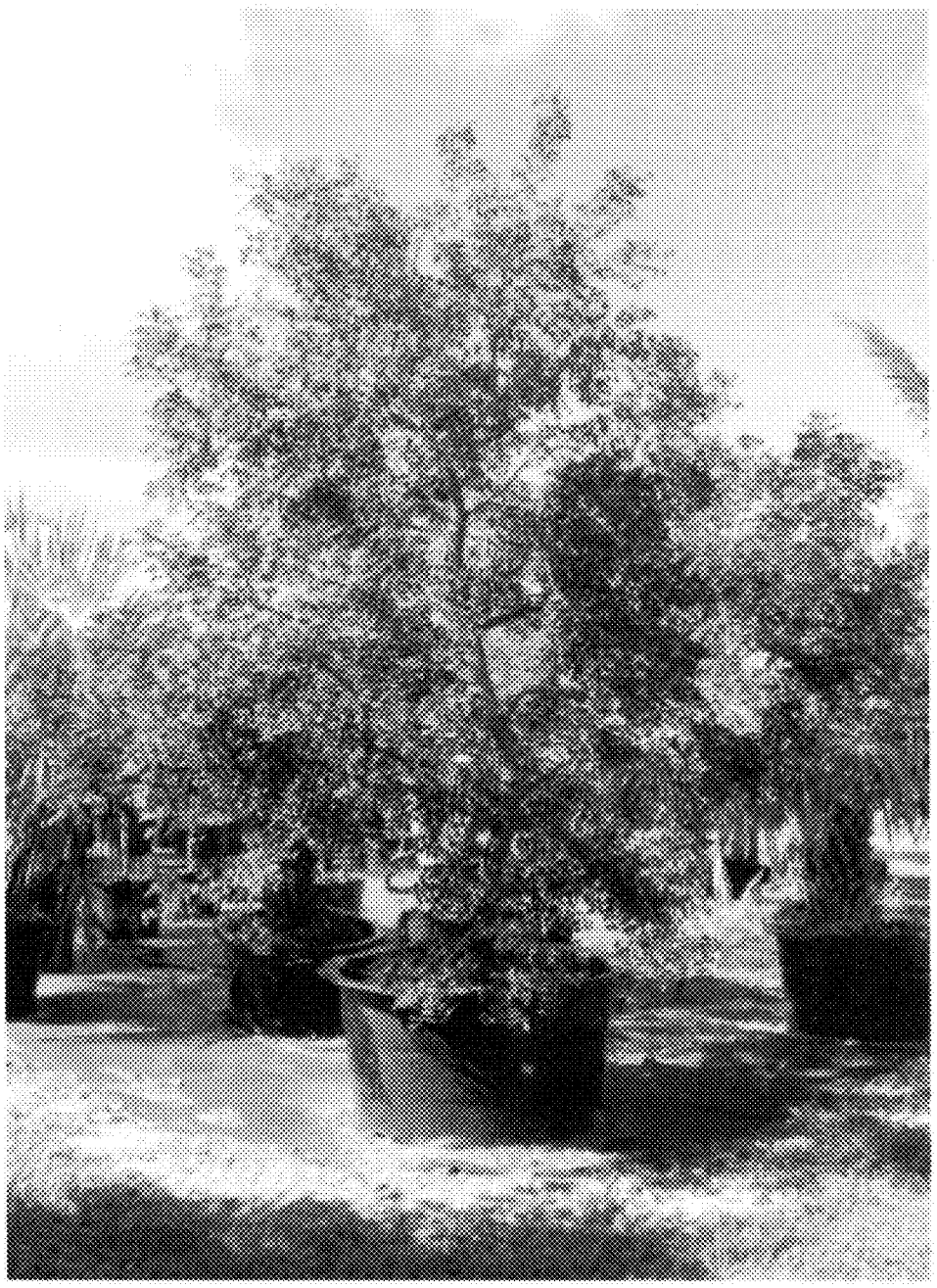
FIG. 1 illustrates the growth habit of 'Ingram's Red'.
Figure 2:
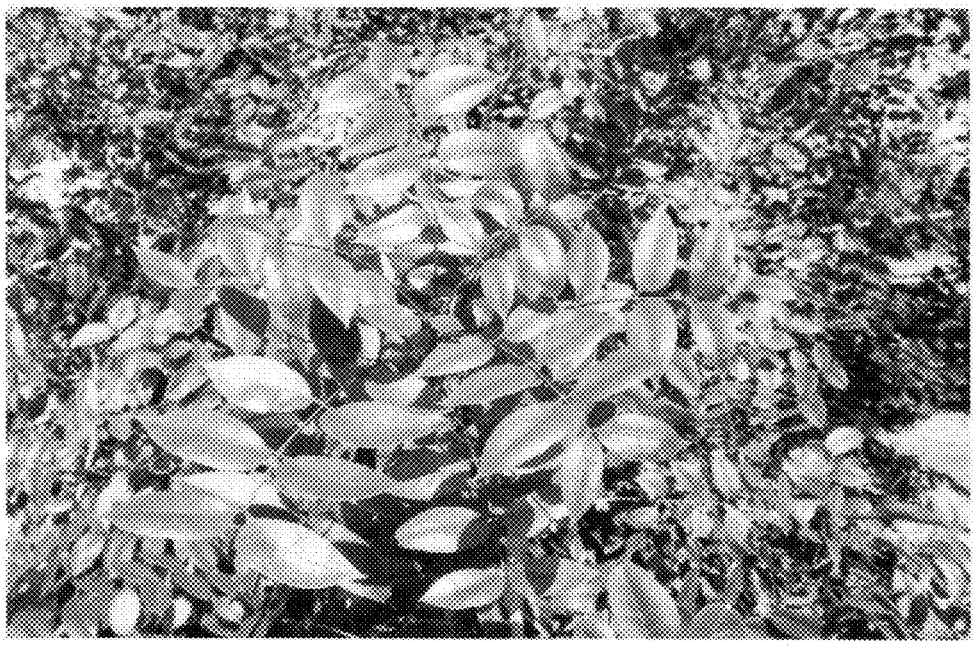

The photograph in FIG. 2 provides a close-up view of the foliage on new growth of 'Ingram's Red'.

The colors in the photograph are as close as possible with the digital photography techniques available, the color values cited in the detailed botanical description accurately describe the colors of the new *Swietenia.*

DETAILED BOTANICAL DESCRIPTION

The following is a detailed description of 1.5 year-old trees of the new cultivar as grown outdoors in 2-gallon containers in Homestead, Fla. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Semi-deciduous.
*Plant habit.*—Dwarf, upright.
*Height and spread.*—Reaches about 3.6 m (12 ft) in height and about 3.6 m (12 ft) in width (11 year-old tree).
*Hardiness.*—U.S.D.A. Zones 10 to 11.
*Diseases.*—No diseases problems have been observed.
*Root description.*—Fibrous, freely branched.
*Propagation.*—Stem cuttings.
*Growth rate.*—Moderate.

Stem description:

*Shape*.—Twigs slightly oval.

*Stem color*.—New growth 166A, maturing twigs closest to 199C with lenticels numerous, small and 199A in color, bark; 199D with striations of 199A.

*Stem size*.—(2-gallon container) Trunk; 2.5 cm in diameter measured 4 cm above soil level, lateral branches average about 6 mm in diameter and 70 cm in length, secondary branches an average of 40 cm in length and 4 mm in width.

*Stem surface*.—Twigs puberulent and dull with numerous small lenticels, mature bark bark-like striations.

*Branching*.—An average of 2 lateral branches and 3 secondary branches per lateral branch.

Foliage description:

*Leaf shape*.—Oval.

*Leaf division*.—Even-pinnate, an average of 4 leaf pairs.

*Leaf fragrance*.—None.

*Leaf internode length*.—1.7 cm.

*Leaflet venation*.—Pinnate, only midrib is conspicuous, lower surface 183A in color, upper surface 199C suffused with 183D.

*Leaflet margins*.—Entire.

*Leaf arrangement*.—Loosely whorled, leaflets are opposite.

*Leaf attachment*.—Petiolate, leaflets petioluled.

*Leaflet surface*.—New foliage; glossy on upper and lower surface, mature foliage; slightly satiny on upper surface and satiny on lower surface.

*Leaf size*.—Average of 12.5 cm in length and 8 cm in width.

*Leaflet size*.—Range from about 3.5 cm in width and 2 cm in width.

*Leaflet internode length*.—An average of 1.5 cm.

*Leaf quantity*.—Average of 11 leafs per 15 cm of lateral branch and 4 leaflets per leaf.

*Leaf color*.—Newly expanded leaves upper surface and lower surface; 187A and changing to N189A suffused with 187A, mature leaves; upper surface N189A and lower surface color147A and suffused with 183C.

*Petioles*.—About 3 cm in length and 1.2 mm in width, 187A in color, glabrous surface with base slightly pubescent.

*Petiolules*.—About 3 mm in length and 1 mm in width, 187A in color, glabrous surface.

*Rachis*.—An average of 11 cm in length (including petiole), 1.5 mm in diameter, glabrous surface with base slightly pubescent, color on young and mature leaves 187A in color.

Inflorescence and fruit description: Flowering has not been observed on the new cultivar, blooms of *Swietenia mahagoni* are small and insignificant and produced in panicles. Fruit of *Swietenia mahagoni* is an ovoid woody capsule, 5 to 10 cm in length and 3 to 6 cm in width, containing numerous winged seeds.

It is claimed:

1. A new and distinct cultivar of *Swietenia* tree named 'Ingram's Red' as herein illustrated and described.

* * * * *